(12) United States Patent
Kao

(10) Patent No.: US 11,399,883 B2
(45) Date of Patent: Aug. 2, 2022

(54) CAUTERIZING DEVICE AND SYSTEM

(71) Applicant: Volta Innovations, S. de R.L. de C.V., Mexquitic de Carmona (MX)

(72) Inventor: Selvin Kao, Ladera Ranch, CA (US)

(73) Assignee: VOLTA INNOVATIONS, S. DE R.L. DE C.V., Mexquitic de (MX)

( * ) Notice: Subject to any disclaimer, the term of this patent is extended or adjusted under 35 U.S.C. 154(b) by 471 days.

(21) Appl. No.: 16/105,860

(22) Filed: Aug. 20, 2018

(65) Prior Publication Data

US 2020/0054381 A1 Feb. 20, 2020

(51) Int. Cl.
- *A61B 18/08* (2006.01)
- *A61B 18/14* (2006.01)
- *A61B 10/02* (2006.01)
- *A61B 18/00* (2006.01)

(52) U.S. Cl.
CPC .......... *A61B 18/08* (2013.01); *A61B 18/1477* (2013.01); *A61B 10/0283* (2013.01); *A61B 2018/00166* (2013.01); *A61B 2018/00172* (2013.01); *A61B 2018/00196* (2013.01); *A61B 2018/00595* (2013.01)

(58) Field of Classification Search
CPC .............. A61B 18/08; A61B 18/00595; A61B 10/0283; A61B 18/1402; A61B 18/1477; A61B 2018/00595; A61B 2018/1412; A61B 2018/00916; A61B 18/04; A61B 2218/007; A61B 16/12
USPC ..................................................... 606/42, 96
See application file for complete search history.

(56) References Cited

U.S. PATENT DOCUMENTS

| | | | |
|---|---|---|---|
| 5,234,428 A | | 8/1993 | Kaufinan |
| 5,246,044 A | * | 9/1993 | Robertson ............ B67D 7/3209 137/312 |
| 5,246,440 A | * | 9/1993 | Van Noord ........ A61B 18/1402 606/39 |
| 5,413,575 A | * | 5/1995 | Haenggi ............ A61B 18/1402 606/39 |
| 5,693,044 A | * | 12/1997 | Cosmescu ............ A61B 18/042 604/35 |
| D535,396 S | | 1/2007 | Reschke et al. |
| 7,172,592 B2 | | 2/2007 | DeSisto |
| 7,879,033 B2 | | 2/2011 | Sartor et al. |
| 8,690,872 B2 | | 4/2014 | Jayaraj |

(Continued)

FOREIGN PATENT DOCUMENTS

WO WO-2008059248 A1 * 5/2008 ............. A61B 18/14

*Primary Examiner* — Linda C Dvorak
*Assistant Examiner* — Lindsay Regan Lancaster
(74) *Attorney, Agent, or Firm* — Innovation Capital Law Group, LLP; Vic Lin

(57) ABSTRACT

An electrocautery device and system include retractability and extension of a cauterizing tip without impacting or applying backpressure to the supporting electrical components inside the device. In some embodiments, a conductive rail is in constant contact with a spring contact electrically coupled to the power source as the cauterizing tip is retracted or extended from the main housing. Some embodiments include a vacuum system that draws fluid from the treatment site during operation. The fluid travels through a passageway that is sealed off from the electrical components by virtue of aspects of the device. Some embodiments include an ergonomic design and are lower cost by using membrane switch circuits instead of a printed circuit board.

18 Claims, 20 Drawing Sheets

(56) References Cited

U.S. PATENT DOCUMENTS

| | | | |
|---|---|---|---|
| 9,023,042 B1 * | 5/2015 | Huron | A61B 18/1402 |
| | | | 606/49 |
| D758,582 S | 6/2016 | Cosmescu | |
| 9,370,394 B2 | 6/2016 | Jayaraj | |
| 9,375,252 B2 * | 6/2016 | Coe | A61B 18/1477 |
| 9,907,621 B2 * | 3/2018 | Jayaraj | A61B 1/00094 |
| 9,987,074 B2 | 6/2018 | Ineson | |
| 10,327,840 B2 | 6/2019 | Ellman | |
| 2003/0029709 A1 | 2/2003 | Serizawa et al. | |
| 2003/0160669 A1 | 8/2003 | Trandafir | |
| 2007/0135812 A1 | 6/2007 | Sartor | |
| 2011/0071520 A1 | 3/2011 | Gilbert | |
| 2013/0032461 A1 | 2/2013 | Jones, Jr. et al. | |
| 2015/0209100 A1 * | 7/2015 | Ineson | A61B 18/1402 |
| | | | 606/42 |
| 2016/0071660 A1 | 3/2016 | Shukla et al. | |
| 2017/0072835 A1 | 3/2017 | Shank et al. | |
| 2018/0243026 A1 | 8/2018 | Park | |
| 2020/0054383 A1 | 2/2020 | Kao | |

* cited by examiner

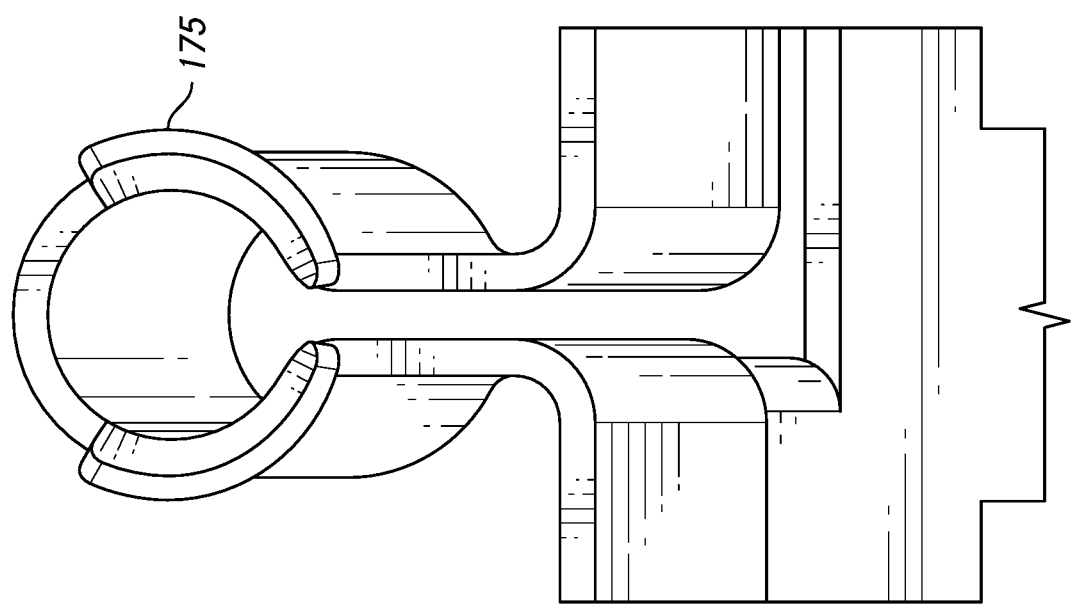

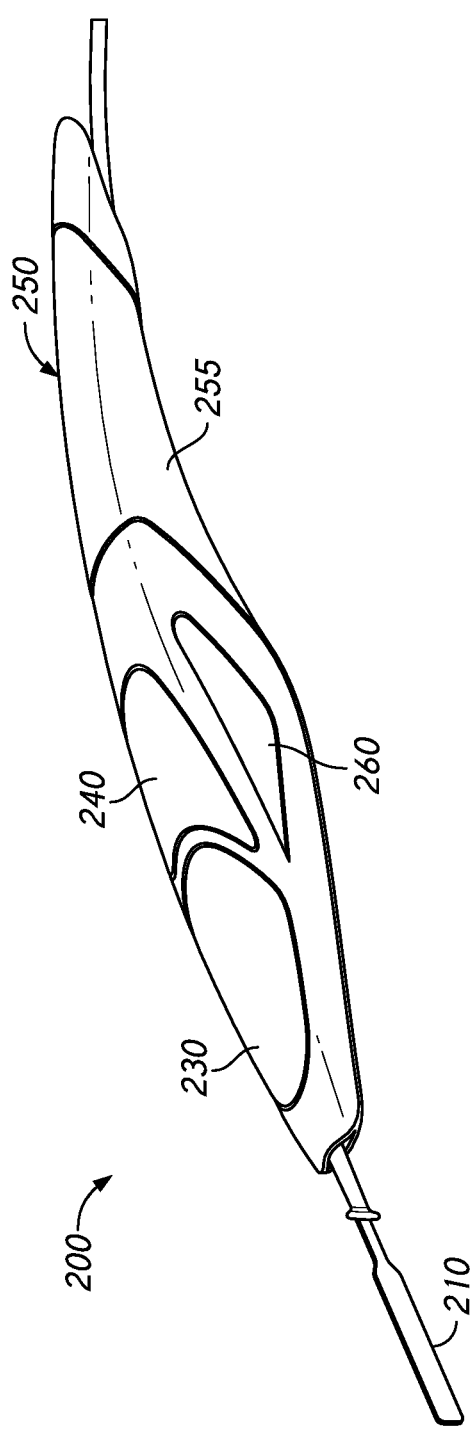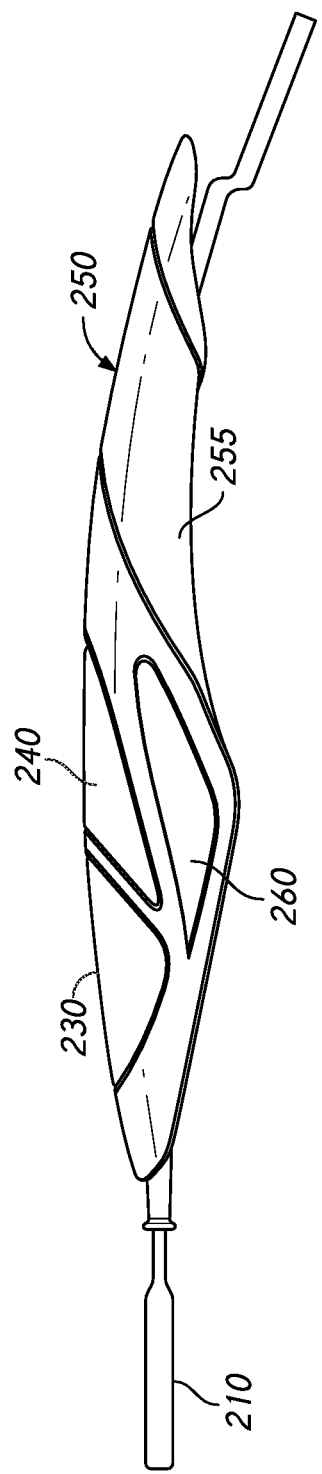
FIG. 15A
FIG. 15B

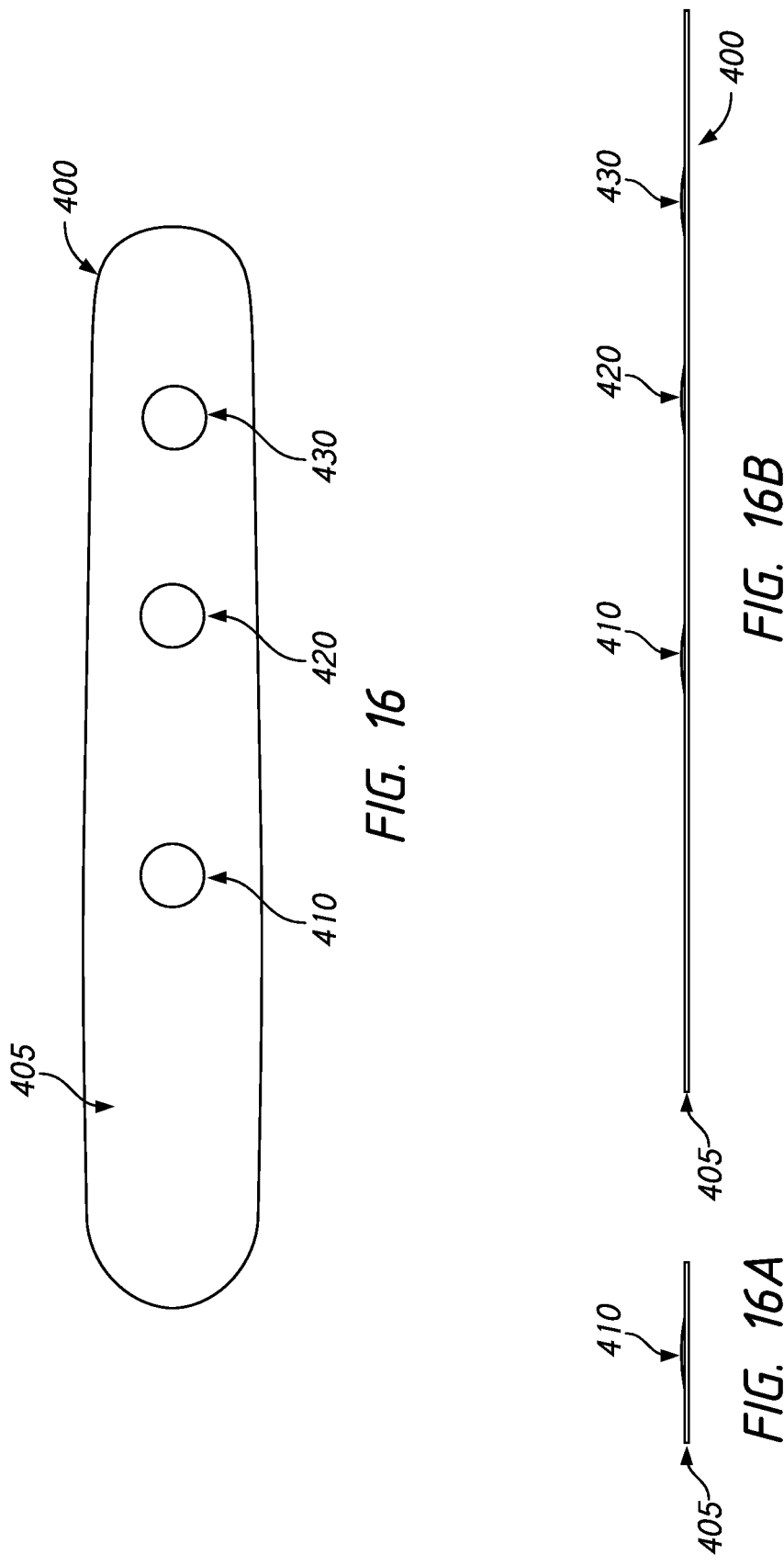

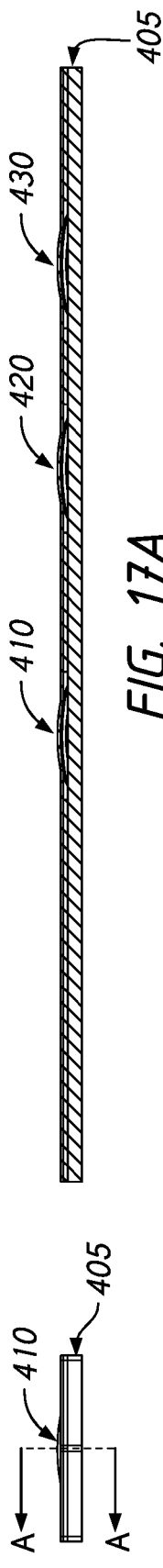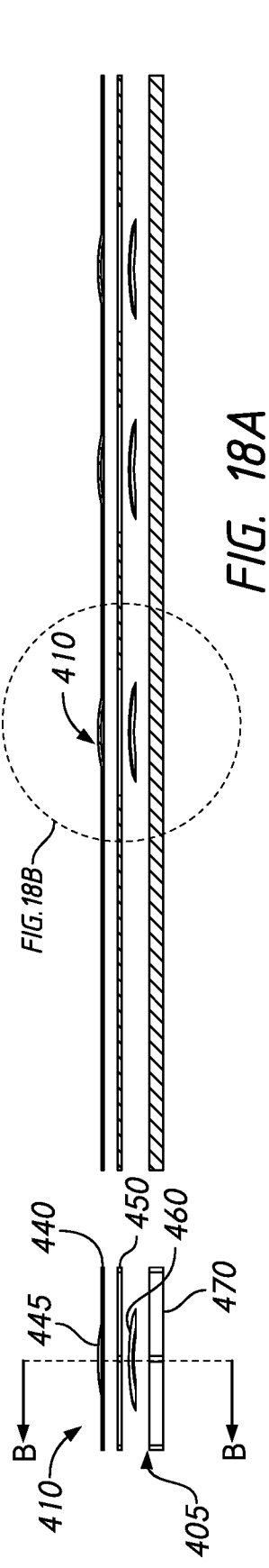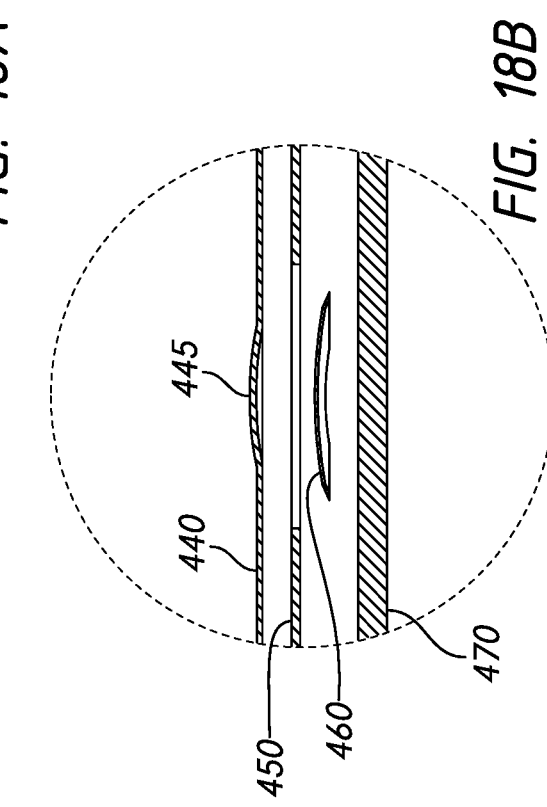

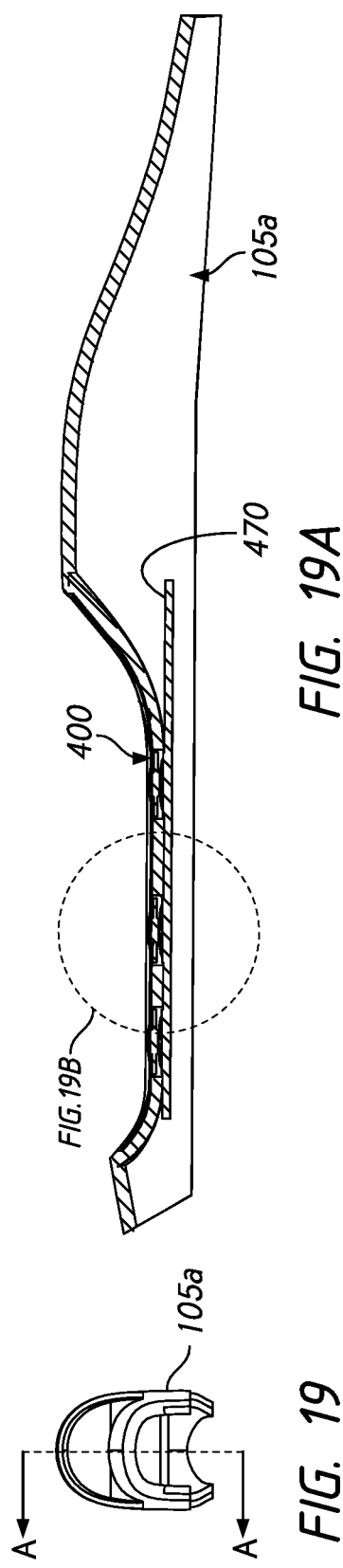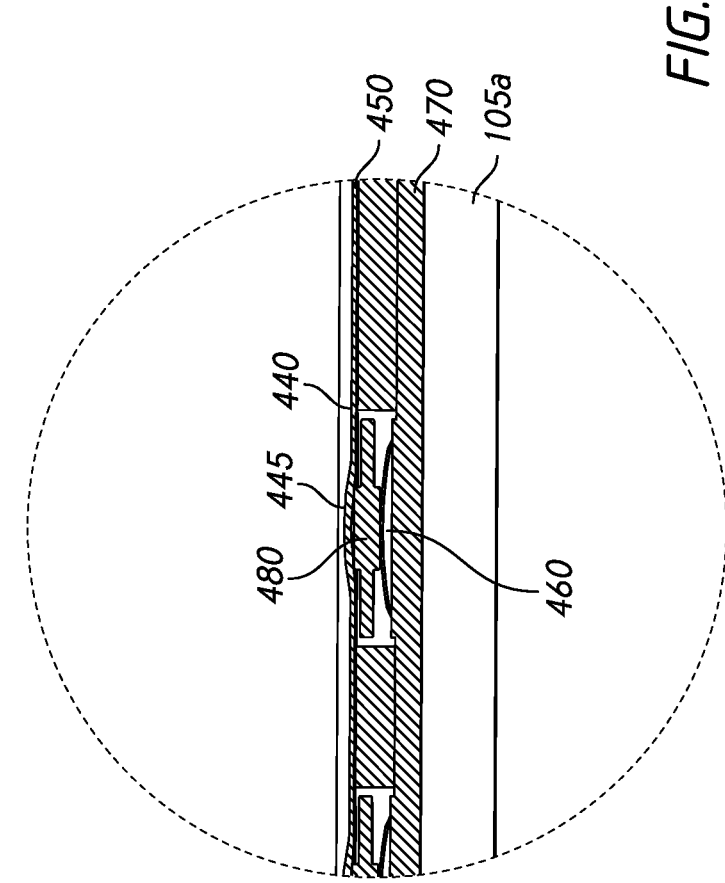

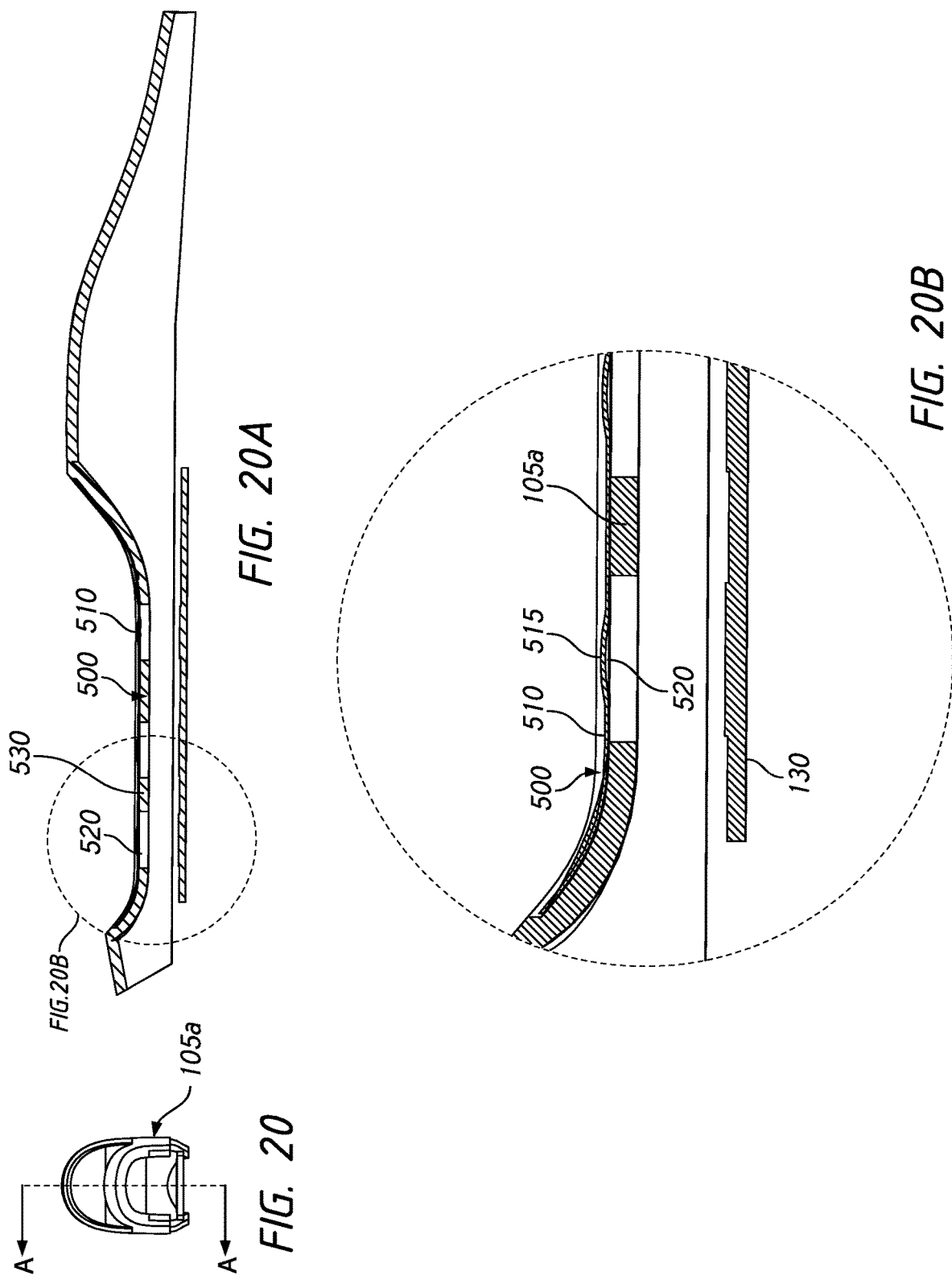

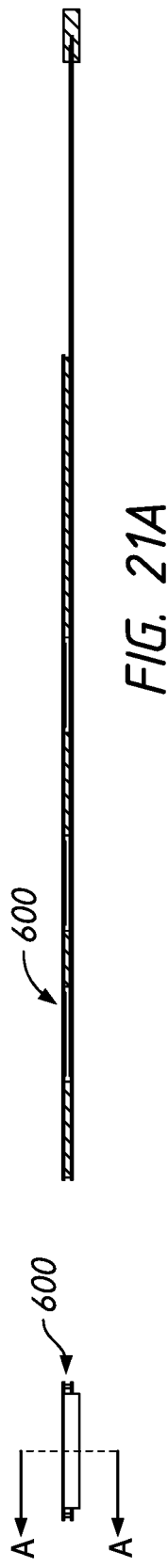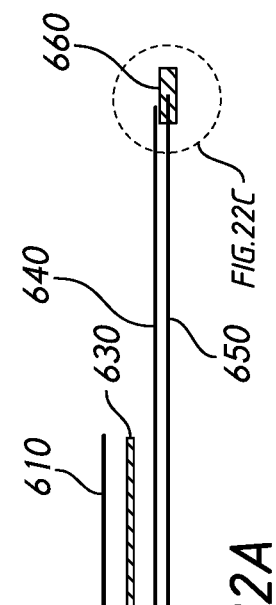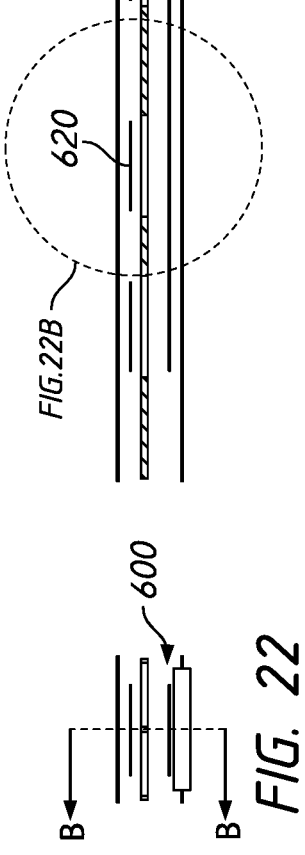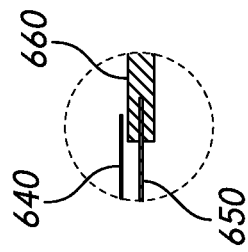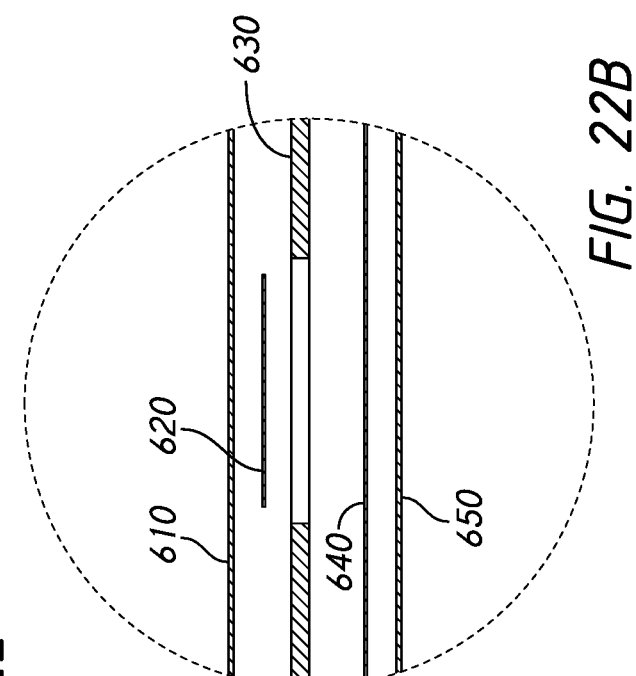

CAUTERIZING DEVICE AND SYSTEM

CROSS-REFERENCE TO RELATED APPLICATION

None.

FIELD OF THE INVENTION

The present invention relates in general to medical devices. More particularly, the invention is directed to cauterizing device and system.

BACKGROUND OF THE INVENTION

During surgery, electrocautery is a technique sometimes used that introduces high frequency current to tissue being treated. An example of a conventional electrocautery pen 50 with a vacuum feature is shown in FIGS. 1 and 2. The conventional electrocautery pen 50 generally includes a vacuum tube 60. In some conventional pens, a cauterizing tip blade tip (not shown) be operated to extend out from the main housing and retract back into the housing. Control buttons 70 and 75 control an operating mode. Button 80 may represent an auxiliary function, for example, triggering a light source (LED).

The vacuum tube 60 in a conventional pen is generally stainless-steel. During a typical operation, fluid (for example smoke or moisture) is drawn through the interior of the stainless-steel vacuum tube 60. As might be appreciated, a stainless-steel tube has a substantial surface area for making conductive contact in the event an electric current in the pen's control system makes contact with the tube. Fluid in the tube may inadvertently create a short circuit. In addition, as might be seen in FIG. 2, some vacuum tubes 60 may have openings through which fluid drawn into the vacuum tube 60 may seep into making inadvertent contact with the electrical components above the tube. This may cause damage to the system and a shock to the user.

Some other conventional electrocautery devices suffer from another problem. As mentioned above, there exist electrocautery pens that are configured to extend and retract a cauterizing tip. However, electrocautery pens with this feature use common shield wiring to connect the cauterizing tip to a PCB. In operation, moving the cauterizing tip back and forth causes back pressure on the PCB connection to the wire. After several uses, the wiring may either damage the PCB or may disconnect from the PCB resulting in device failure.

Accordingly, a need exists for an electrocautery system that can safely vacuum fluid from a surgical site while maintaining a reliable electrical connection between the cauterizing tip and the control board when extending or retracting the cauterizing tip.

SUMMARY OF THE INVENTION

In a first aspect, an electrocautery system comprises a rear base tube; a slider tube coupled to the rear base tube, wherein the slider tube is configured to telescope toward a front nozzle tube or away from the rear base tube; a metal spring contact mounted to either the front nozzle tube or the rear base tube; a conductive rail mounted to the slider tube, wherein the metal spring contact is disposed to make constant contact with the conductive rail as the slider tube telescopes toward or away from the rear base tube; a mount on a distal end of the conductive rail, the mount configured to receive a cauterizing tip; and a power line in electrical communication with the metal spring contact, the conductive rail, and the mount for providing power to the cauterizing tip during operation of the electrocautery system.

In a second aspect, an electrocautery system comprises a rear base tube; a slider tube coupled to the rear base tube, wherein the slider tube is configured to telescope toward a front nozzle tube or away from the rear base tube; a metal spring contact mounted to either the front nozzle tube or the rear base tube; a conductive rail mounted to the slider tube, wherein the metal spring contact is disposed to make constant contact with the conductive rail as the slider tube telescopes toward or away from the rear base tube; a mount on a distal end of the conductive rail, the mount configured to receive a cauterizing tip; a fluid passage through the distal end of the slider tube to a proximal end of the rear base tube and a power line in electrical communication with the metal spring contact, the conductive rail, and the mount for providing power to the cauterizing tip during operation of the electrocautery system.

In a third aspect, an electrocautery system comprises a rear base tube; a slider tube coupled to the rear base tube, wherein the slider tube is configured to telescope toward a front nozzle tube or away from the rear base tube; a static metal contact mounted to either the front nozzle tube or the rear base tube; an elongated metal contact mounted to the slider tube, wherein the static metal contact is disposed to make constant contact with the elongated metal contact as the slider tube telescopes toward or away from the rear base tube; a mount on a distal end of the slider tube, the mount configured to receive a cauterizing tip; a conductive connection between the cauterizing tip and the elongated metal contact; and a power line in electrical communication with the static metal contact, the elongated metal contact, and the mount for providing power to the cauterizing tip during operation of the electrocautery system.

These and other features and advantages of the invention will become more apparent with a description of preferred embodiments in reference to the associated drawings.

DESCRIPTION OF THE DRAWINGS

FIG. 14 is a partial, bottom, rear perspective view of the cauterizing tip mount and conductive rail of FIG. 11.

FIG. 15A is a top perspective view of an electrocautery system according to another embodiment.

FIG. 15B is a side view of the system of FIG. 15A.

FIG. 16 is a top view of a switch system for an electrocautery system according to another embodiment.

FIG. 16A is an end view of the switch of FIG. 16.

FIG. 16B is a side view of the switch of FIG. 16.

FIG. 17 is an end view of an overlay assembly for a single switch of FIG. 16A.

FIG. 17A is a cross-sectional view taken along the line A-A of FIG. 17.

FIG. 18 is an exploded view of the overlay assembly of FIG. 17.

FIG. 18A is a cross-sectional view taken along the line B-B of FIG. 18.

FIG. 18B is an enlarged view of the area within the circle of FIG. 18A.

FIG. 19 is an end view of an overlay switch system according to another embodiment.

FIG. 19A is a side view of the system of FIG. 19.

FIG. 19B is an enlarged view of the area within circle B of FIG. 19A.

FIG. 20 is an end view of an overlay switch assembly according to an embodiment.

FIG. 20A is a cross-sectional side view of the membrane switch assembly of FIG. 20.

FIG. 20B is an enlarged view of the area within the circle of FIG. 20A.

FIG. 21 is an end view of membrane switch system on an electrocautery device according to an embodiment.

FIG. 21A is a cross-sectional view taken along the line A-A of FIG. 21.

FIG. 22 is an exploded view of the membrane switch assembly of FIG. 21.

FIG. 22A is a cross-sectional side view of the membrane switch assembly of FIG. 22.

FIG. 22B is an enlarged view of the area within the circle FIG. 22B of FIG. 22A.

FIG. 22C is an enlarged view of the area within the circle FIG. 22C of FIG. 22A.

DETAILED DESCRIPTION OF THE PREFERRED EMBODIMENTS

The following preferred embodiments, in general, are directed to a device and system for electrocautery procedures. As will be appreciated, aspects of the device and its embodiments provide a reliable electrical connection for the cauterizing tip in embodiments that telescope the tip from the housing. Other aspects help prevent inadvertent electrical shocks or short circuits by preventing fluid being vacuumed away from the procedure site from entering parts of the system that have electrical components.

In other aspects, the disclosure describes an electrocautery device and system that provides a more comfortable tool that helps the user during long procedures. Embodiments may include a housing with membrane circuit-based switch(es) and no PCB nor additional features besides the cut and coagulation (to keep cost down).

Figure 1:
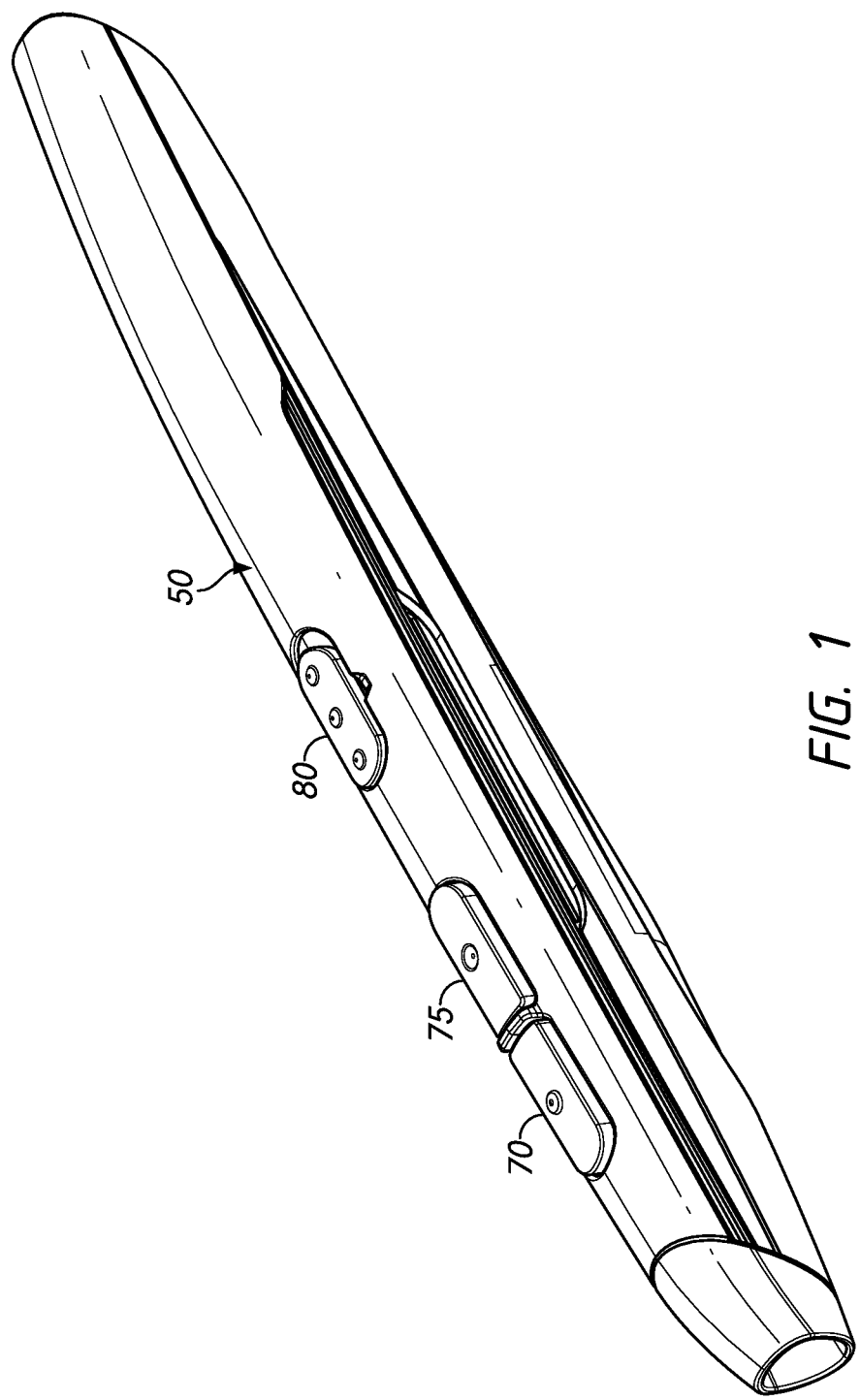
FIG. 1 is a perspective view of a conventional cautery pen with vacuum tube.
Figure 2:
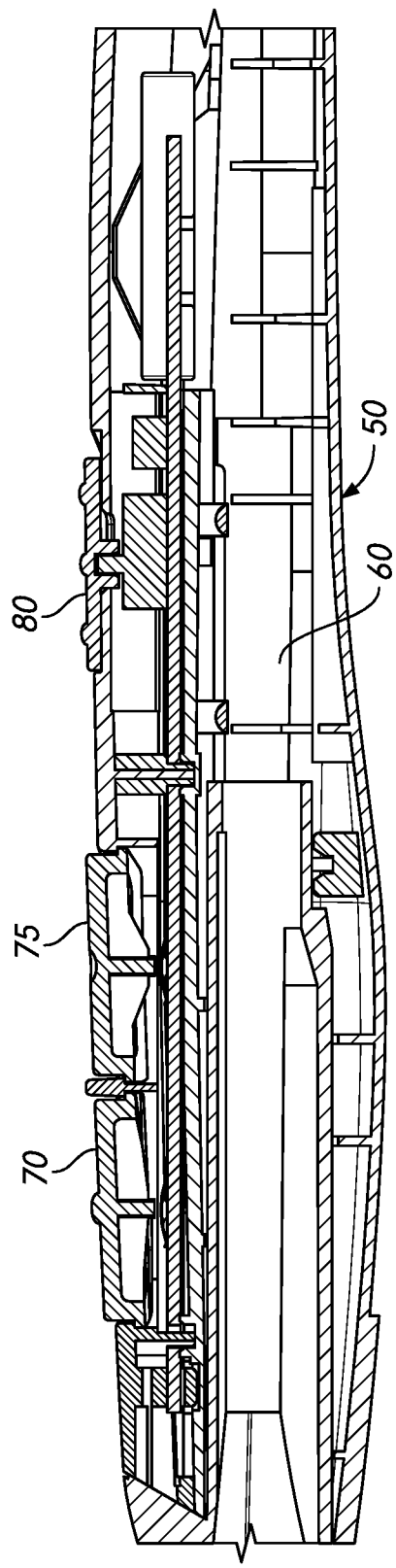
FIG. 2 is a cross-sectional view of the cautery pen and vacuum tube of FIG. 1.
Figure 3A:
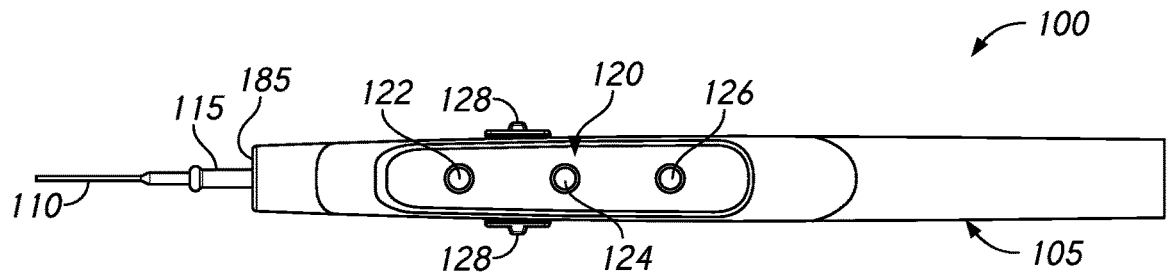
FIG. 3A is a top view of an electrocautery system according to an embodiment of the subject technology.

Referring now to FIG. 3A, an electrocautery device 100 (sometimes referred to simply as the "device 100") is shown according to an exemplary embodiment. Only the exterior of the device 100 is shown which includes in general a main casing 105 and a cauterizing tip 110 which may retract into/extend from the main casing 105 during operation (for example, when applying a current through the cauterizing tip 110 to tissue being treated). Reference to a "distal end" is generally referring to the end of the device 100 that is towards the cauterizing tip 110. The cauterizing tip 110 may be mounted to a tip sleeve 115. In some embodiments, the cauterizing tip 110 may include a blade edge 112. In some embodiments, the cauterizing tip 110 is part of the system and in some embodiments, the device 100 does not include the cauterizing tip 110, which is replaceable between procedures. Some embodiments include a slider switch 128 coupled to the cauterizing tip 110 to extend or retract the cauterizing tip 110 as desired from a nozzle 185. A control panel 120 may include a plurality of buttons 122, 124, and 126 for operating different modes/functions of the device 100.

Figure 3B:
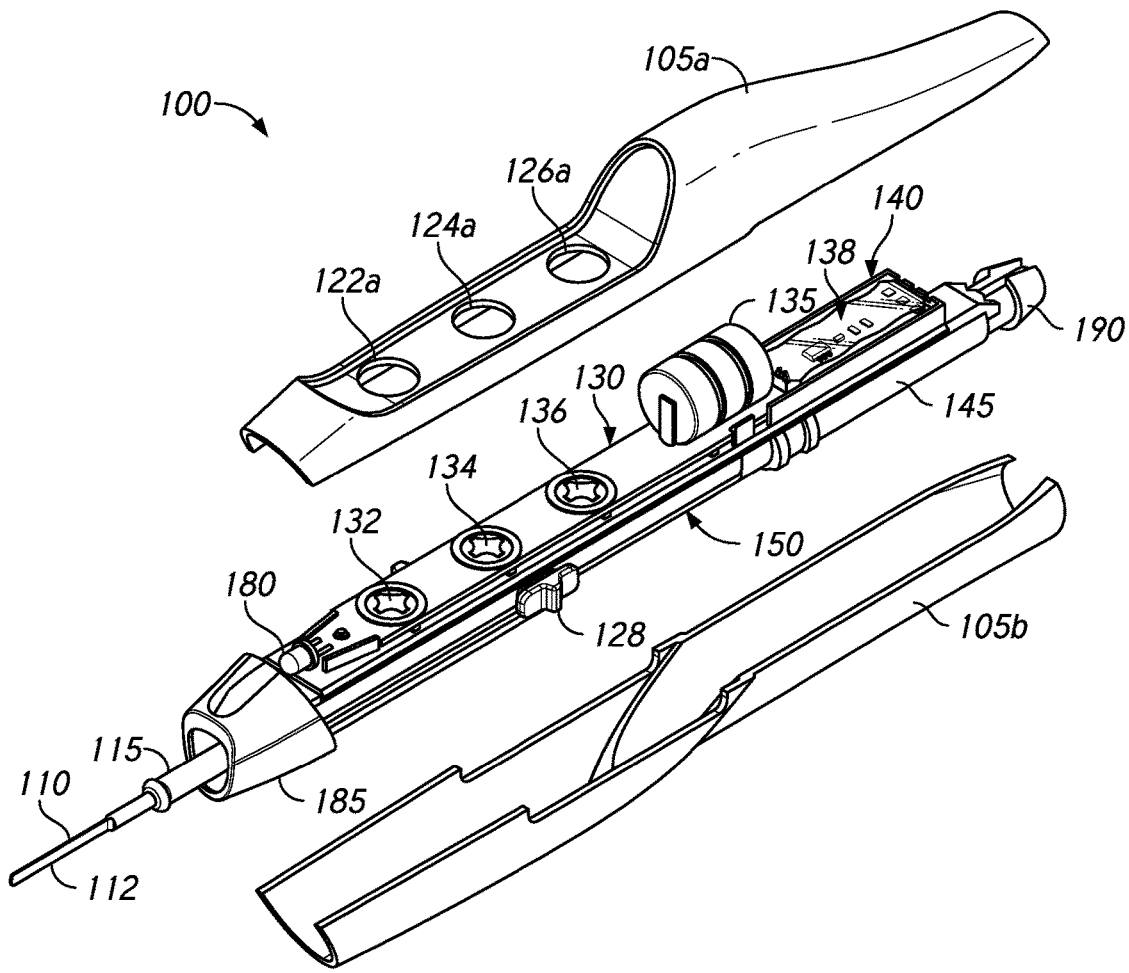
FIG. 3B is an exploded top perspective view of the system of FIG. 3A.

With continued reference to the exterior of the device 100, FIG. 3B shows a main casing 105 which may comprise upper half 105a and lower half 105b encasing mechanical and electrical support elements. The mechanical elements include generally, a rear base tube 145, a slider tube 150, and a PCB tray 140 (which elements will be discussed with reference to FIGS. 4-6). The electrical elements generally include a conductive rail 170 and a metal spring contact 160 (the two of which will be discussed with reference to FIGS. 4-5), PCB 130 (FIGS. 7 and 8), and button elements (discussed in reference to FIGS. 7-10).

Referring now to FIGS. 3B-10, details of the internal assembly of the device 100 will be described. The reader should constantly refer back to FIG. 3B in the description that follows with concurrent reference to specific figures showing features in focus.

Figure 4:
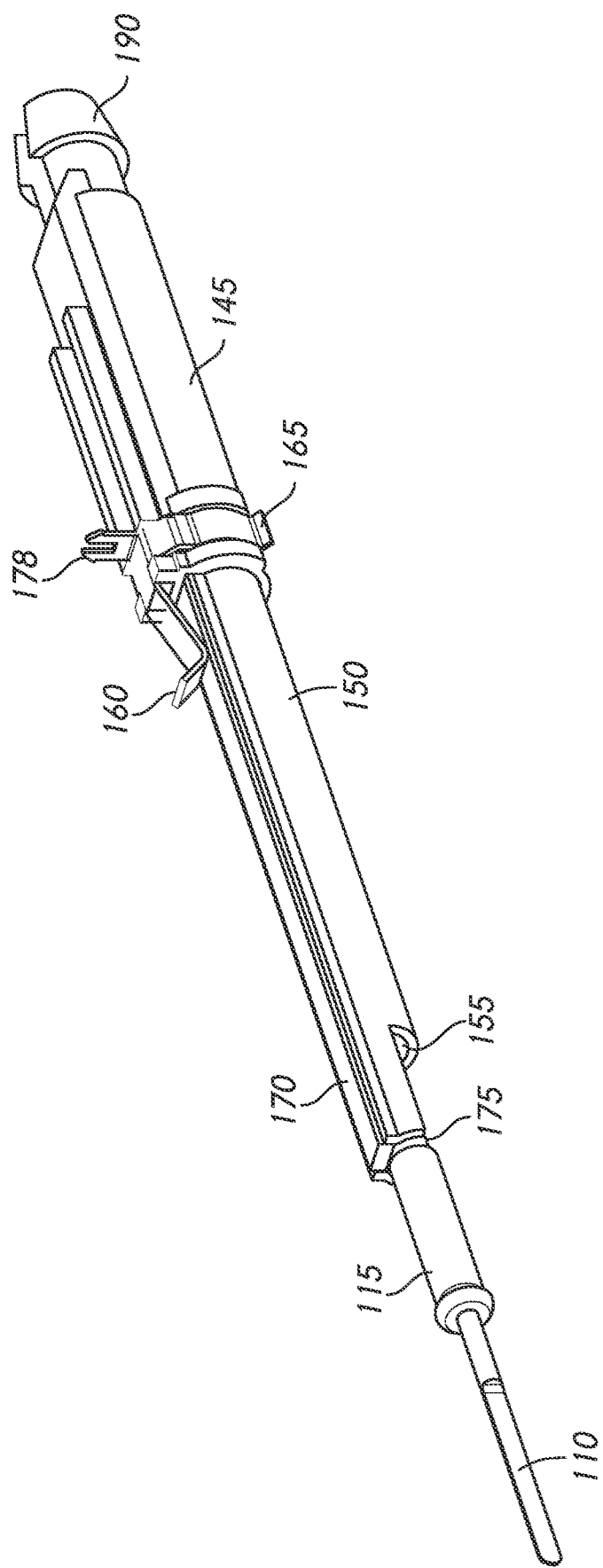
FIG. 4 is a perspective top view of an internal assembly of the system of FIG. 3B sans electrical elements according to an embodiment of the subject technology.
Figure 5:
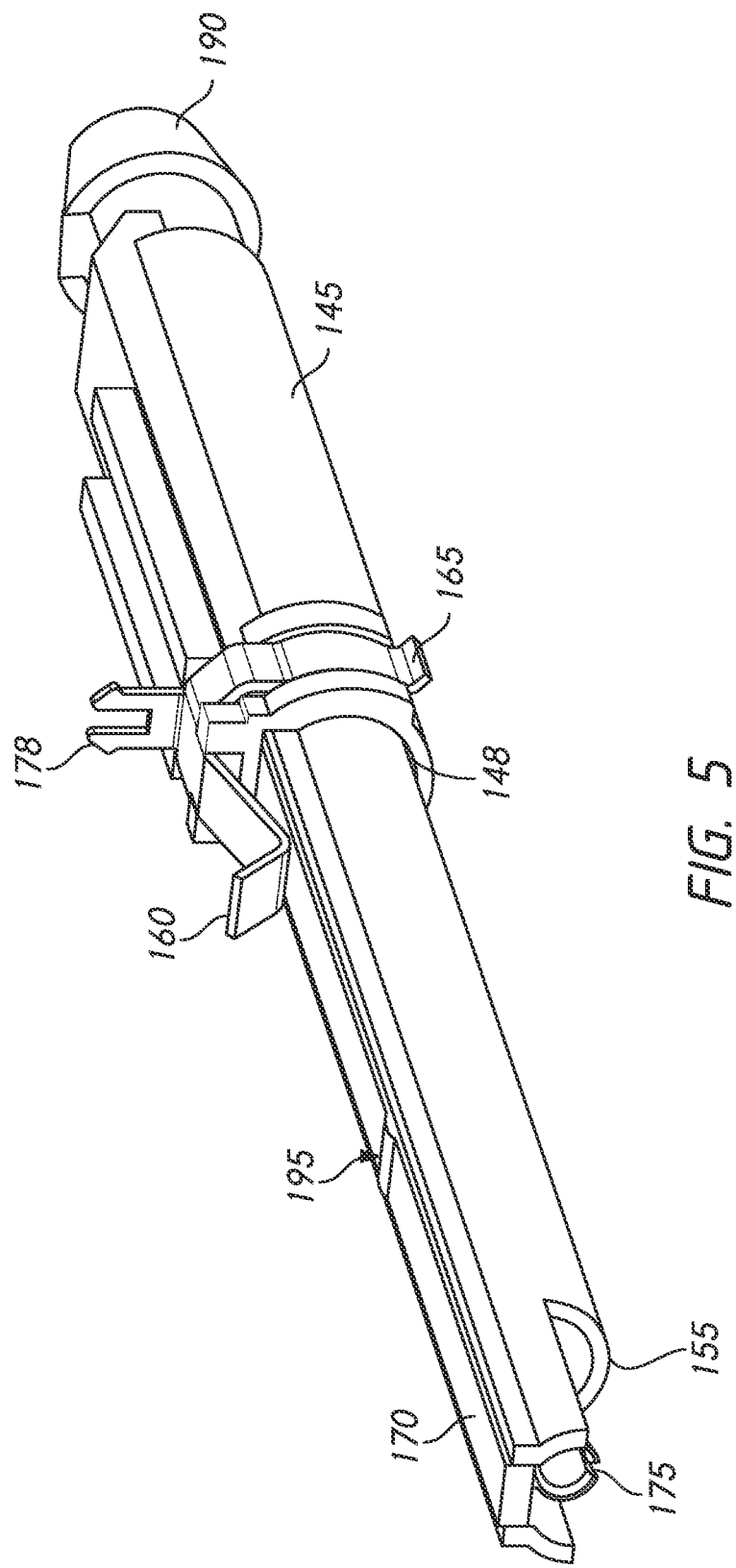
FIG. 5 is an enlarged view of the internal assembly of FIG. 4 sans the cauterizing tip.

Referring now to FIGS. 4 and 5, a portion of the internal assembly of the device 100 is shown in detail with focus on the rear base tube 145, the slider tube 150, the metal spring contact 160, and the conductive rail 170. In an exemplary embodiment, the rear base tube 145 is hollow. Reference to a "proximal end" of the device 100 is generally meant to refer to a rear end of the rear base tube 145 which is on the opposite end of the device 100 from the cauterizing tip 110. The rear base tube 145 may in some embodiments include an outlet port 190 that connects to a vacuum source (not shown) for embodiments which include a vacuum feature. In an exemplary embodiment, the rear base tube 145 and the slider tube 150 may comprise non-conductive material such as plastic. In addition, the rear base tube 145 and the slider tube 150 may be one-piece injected molded and do not have openings to the elements exterior to each respectively. In some embodiments, the slider switch 128 may be integrated into the body of slider tube 150. The slider tube 150 may similarly be hollow (like rear base tube 145), so that when connected to the rear base tube 145, forms a fluid passage 155 (sometimes referred to as a vacuum channel), that extends from the distal end of the slider tube 150 through the outlet port 190. In operation, as the device 100 is used and smoke from the site appears, the vacuum source may be activated to draw fluid into the vacuum channel 155 through the outlet 190 and out of the device 100 to keep the area free of for example, smoke that may bother the surgeon. It will be appreciated that the rear base tube 145 and slider tube 150 seal the electrical elements of the device 100 from the fluid passing within the fluid passage 155. In addition, in an exemplary embodiment, the slider tube 150 is configured to telescope from the rear base 145. In the embodiment shown, the slider tube 150 is configured to slide within the interior of the rear base 145. However, other embodiments may configure the slider tube 150 to slide over the exterior of the rear base 145.

In an exemplary embodiment, the device 100 includes a conductive rail 170 mounted to an exterior surface of the slider tube 150. As shown, this may be the upper or top surface of the slider tube 150. The conductive rail 170 may be an elongated metal contact that in some embodiments extends from approximately the distal end to approximately the proximal end of the slider tube 150. In an exemplary embodiment, the conductive rail 170 is wholly exterior of the fluid passage 150. Referring concurrently to FIGS. 11-14, which show enlarged views of the conductive rail 170, in an exemplary embodiment, the conductive rail 170 may be an elongated flat bar 310 of metal (for example, stainless steel), which may include a flat proximal end 320 and a mount 175 on the distal end for receiving the cauterizing tip 110. The conductive rail 170 may include notches 330 that index the rail to tabs (not shown) on the slider tube 150 which affixes the conductive rail 170 into place. The mount 175 may be conductive so that when the cauterizing tip 110 is mounted, a current passes through the conductive rail 170 to the cauterizing tip 110 for operation of the cauterizing tip 110. In some embodiments, the mount 175 may not necessarily be conductive but a conductive connection may be positioned to contact the cauterizing tip 110 and simultaneously contact the conductive rail 170. Yet, even though the cauterizing tip 110 is able to access current through the mount 175 and conductive rail 170, it will be appreciated that the fluid drawn into the passage 155 remains out of contact with the conductive rail 170. In addition, in some embodiments, the conductive rail 170 may include break points 195 which may be for example, non-conductive bumps or pits that when slid under the metal spring contact 160, will interrupt current at that point. The break points 195 may be positioned so that a marking or other indicator on the device 100 will show where to position the slider switch 128 for a temporary non-operational state of the device 100.

In an exemplary embodiment, the metal spring contact 160 is attached to the rear base tube 145 and disposed to maintain constant contact with the conductive rail 170. The metal spring contact 160 may be static relative to the conductive rail 170 which moves as the slider tube 150 telescopes toward or away from the rear base tube 145. The metal spring contact 160 may be for example, a piece of stainless steel (or other metal) projection that is bent downward with a tip (or as shown a nadir of a bent tip) that is positioned into contact with a top surface of the conductive rail 170. In some embodiments, the metal spring contact 160 includes a clip 165 that affixes the spring to an exterior of the rear tube 145 and prevents the metal spring contact 160 from moving. In an exemplary embodiment, a pair of prongs 178 may project upward from the clip 165, which will be used to pass current from the power source. As will be appreciated, movement of the conductive rail 170 as the device telescopes does not place any backpressure onto the metal spring contact 160. Accordingly, current passing through the metal spring contact 160 will flow uninterrupted during the telescoping process and will remain reliably connected to the power line that flows through the PCB 130 to the metal spring contact 160.

Figure 6:
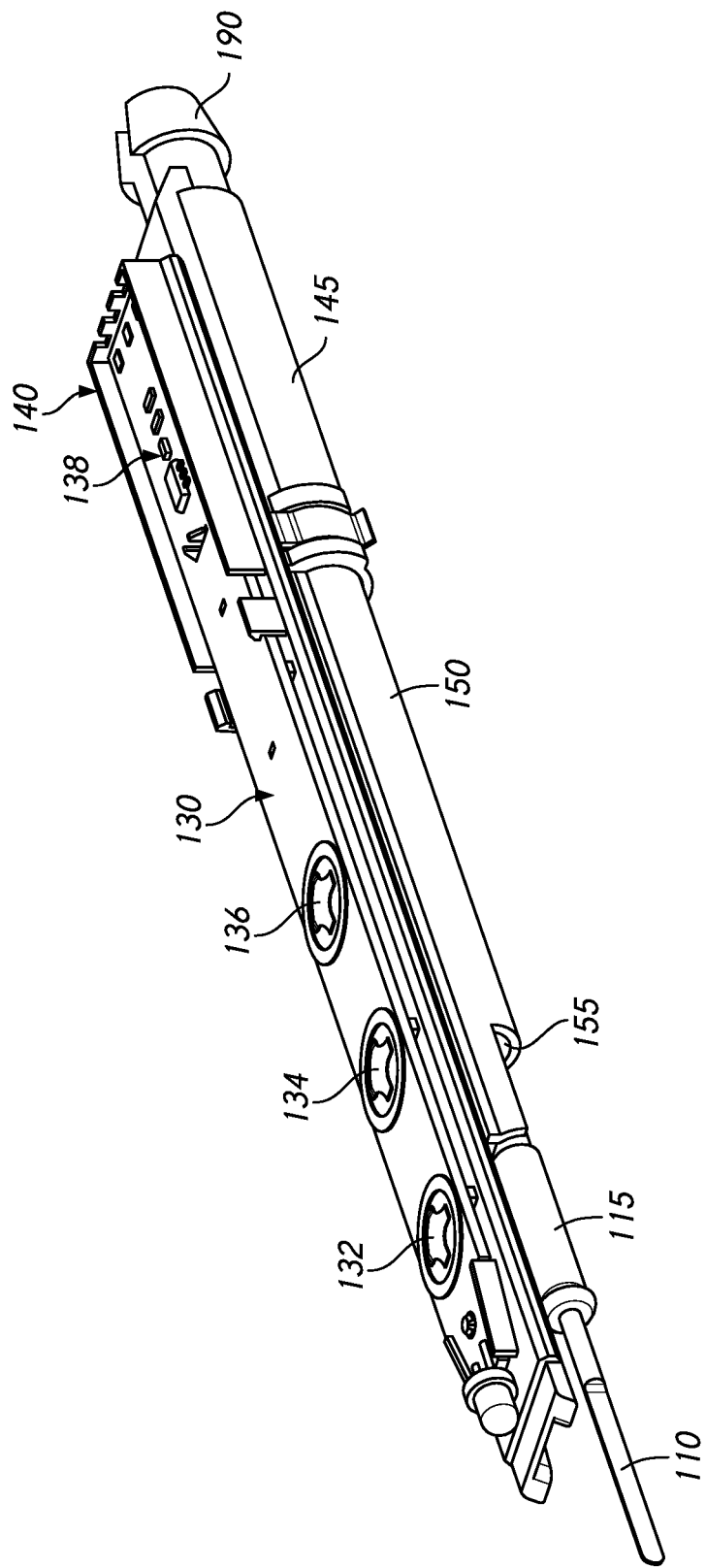
FIG. 6 is a perspective top view of the internal assembly of the system of FIG. 4 including a tray for holding electrical components.

Referring now to FIG. 6, the rear base tube 145, slider tube 150, metal spring contact 160 and conductive rail 170 are covered by a PCB tray 140 that is configured to hold the PCB 130. Numerous tabs and blocks (unnumbered are shown which will index the PCB 130 to the tray 140. The pair of prongs 178 project upward through holes in the tray 140 and will form a connection with the power line in PCB 130. It will be understood that the main power line that provides power to the cauterizing tip 110 may come from an external source (such as power from an outlet), and for sake of illustration, an actual wire being connected to the device 100 and the connection to the PCB 130 is omitted, however it is readily understood by those in the art to connect power to the power line in the system.

Figure 7:
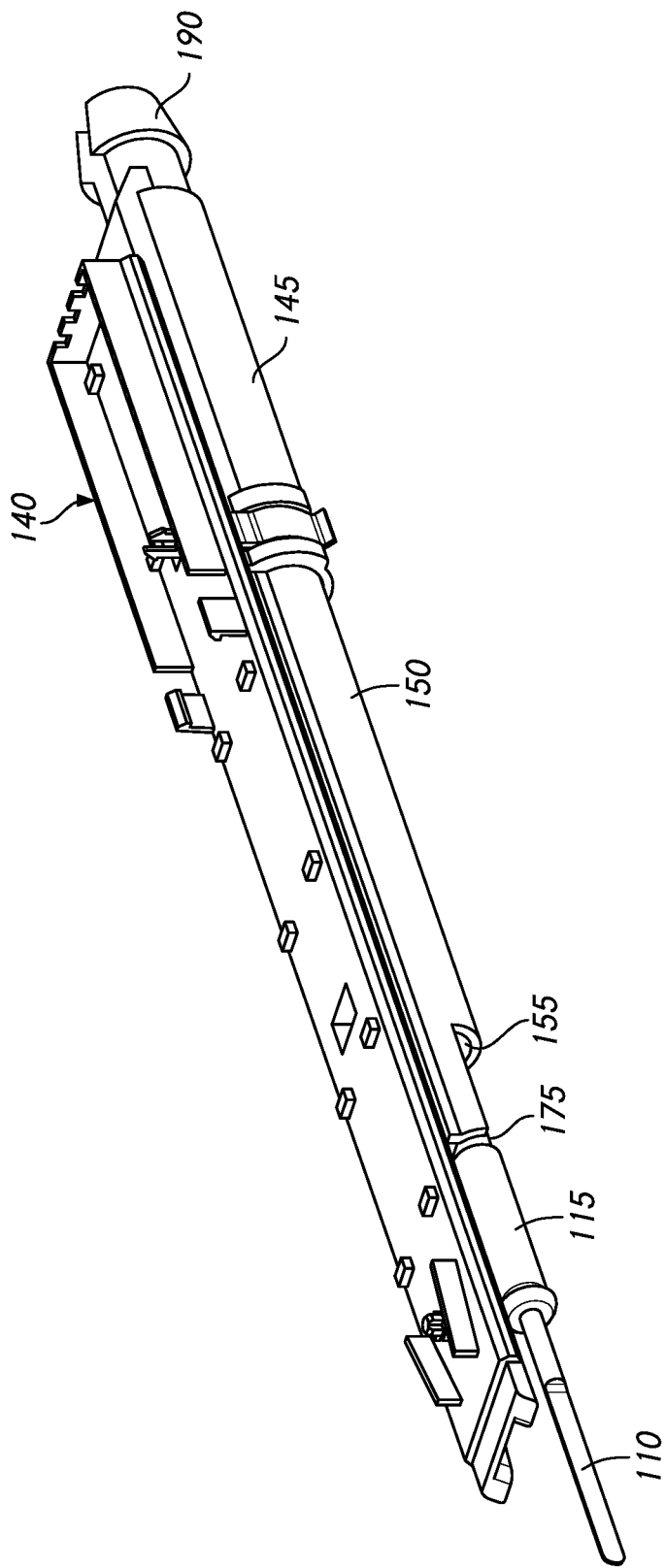
FIG. 7 is a perspective top view of the internal assembly of FIG. 3B sans a PCB and battery.

Referring now to FIG. 7, the PCB 130 is shown positioned within the tray 140. The pair of prongs 178 may be soldered into contact with traces (not shown) in the PCB 130. Some embodiments may include a controller 138 which directs operation of the current from the power source to the metal spring contact 160 and through to the cauterizing tip 110 based on the recognition of one of the different buttons being pressed.

Figure 8:
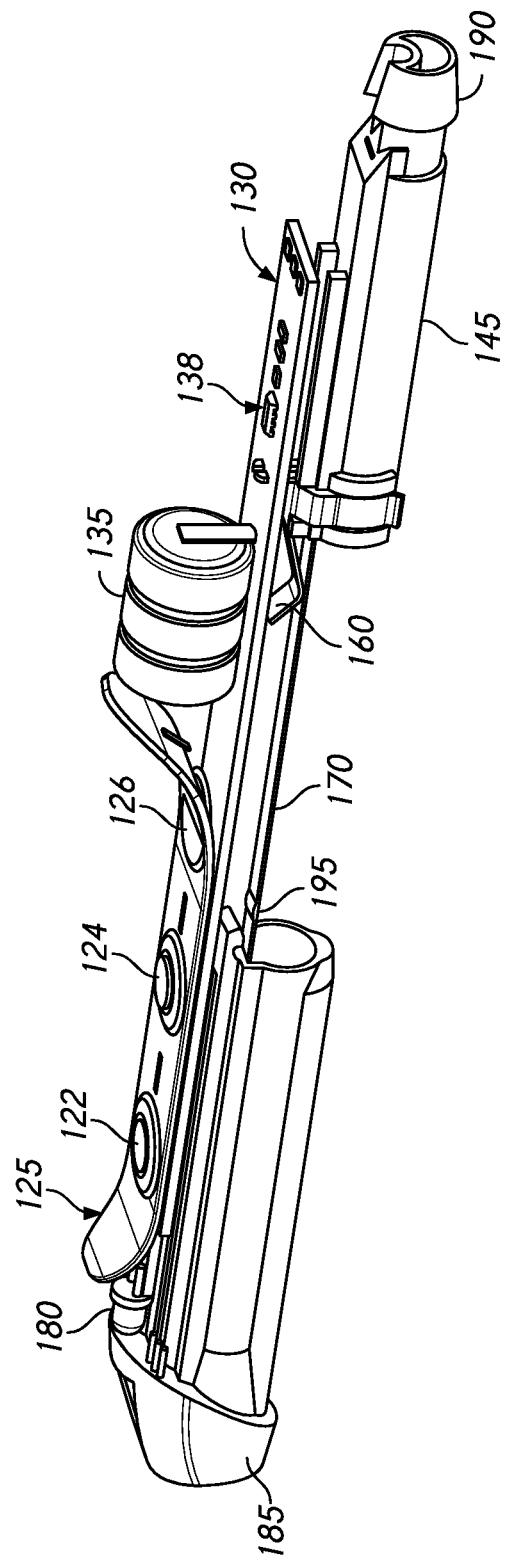
FIG. 8 is a perspective side view of the internal assembly of FIG. 3B sans a slider tube.

Referring to FIG. 8, the internal assembly being built up is shown with the slider tube 150 being omitted between the rear base tube 145 and the nozzle 185 and the tray 140 omitted for sake of clarity in the illustration. In an exemplary embodiment, the PCB 130 may also include button switch pads 132, 134, and 136 and a battery 135 to power an L. E. D. 180 (shown in FIGS. 3B, 7 and 8). The L. E. D. 180 may illuminate a transparent portion on the nozzle 185.

Figure 9:
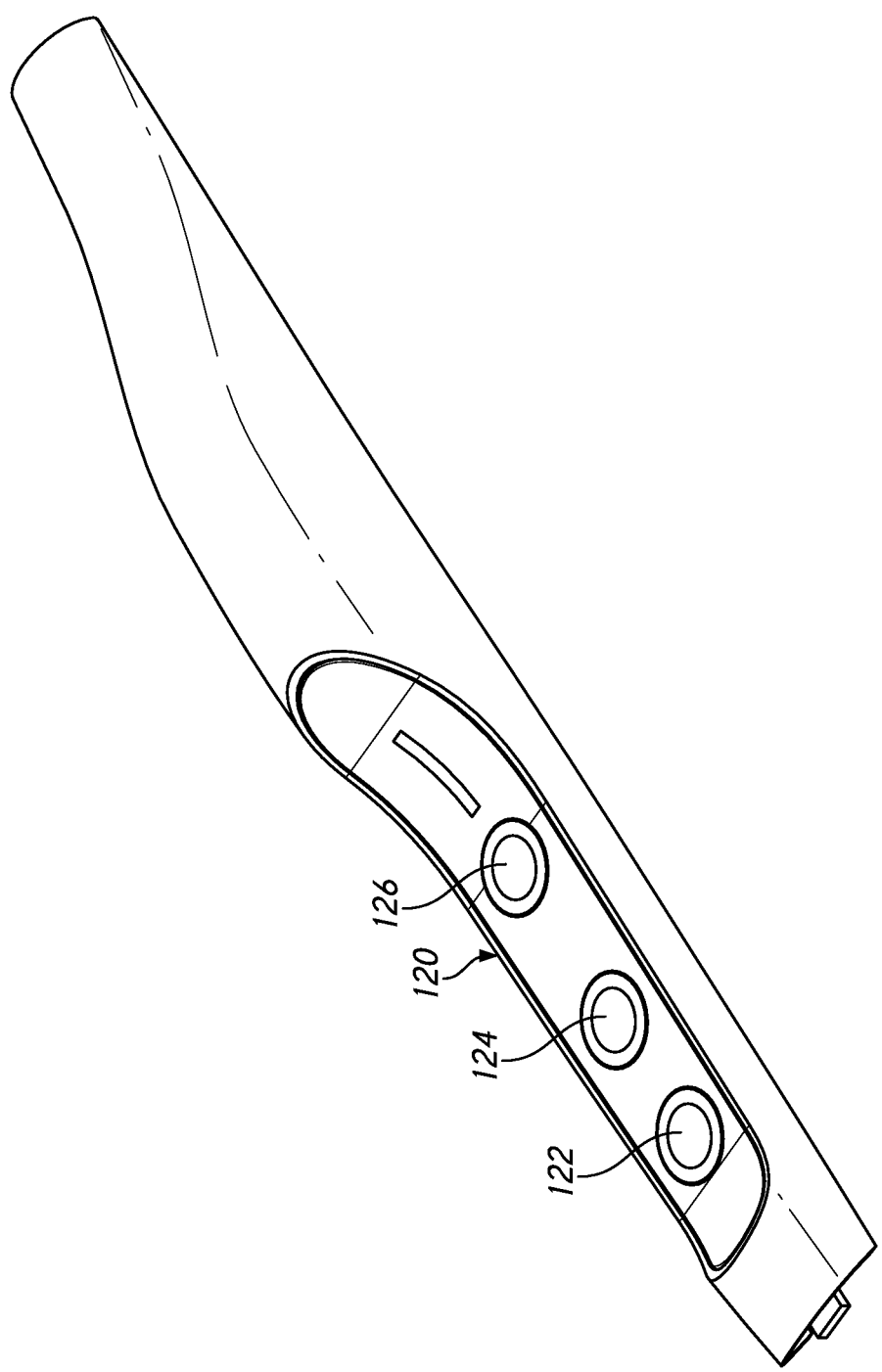
FIG. 9 is a top perspective view of an upper shell of the system of FIG. 3A.
Figure 10:
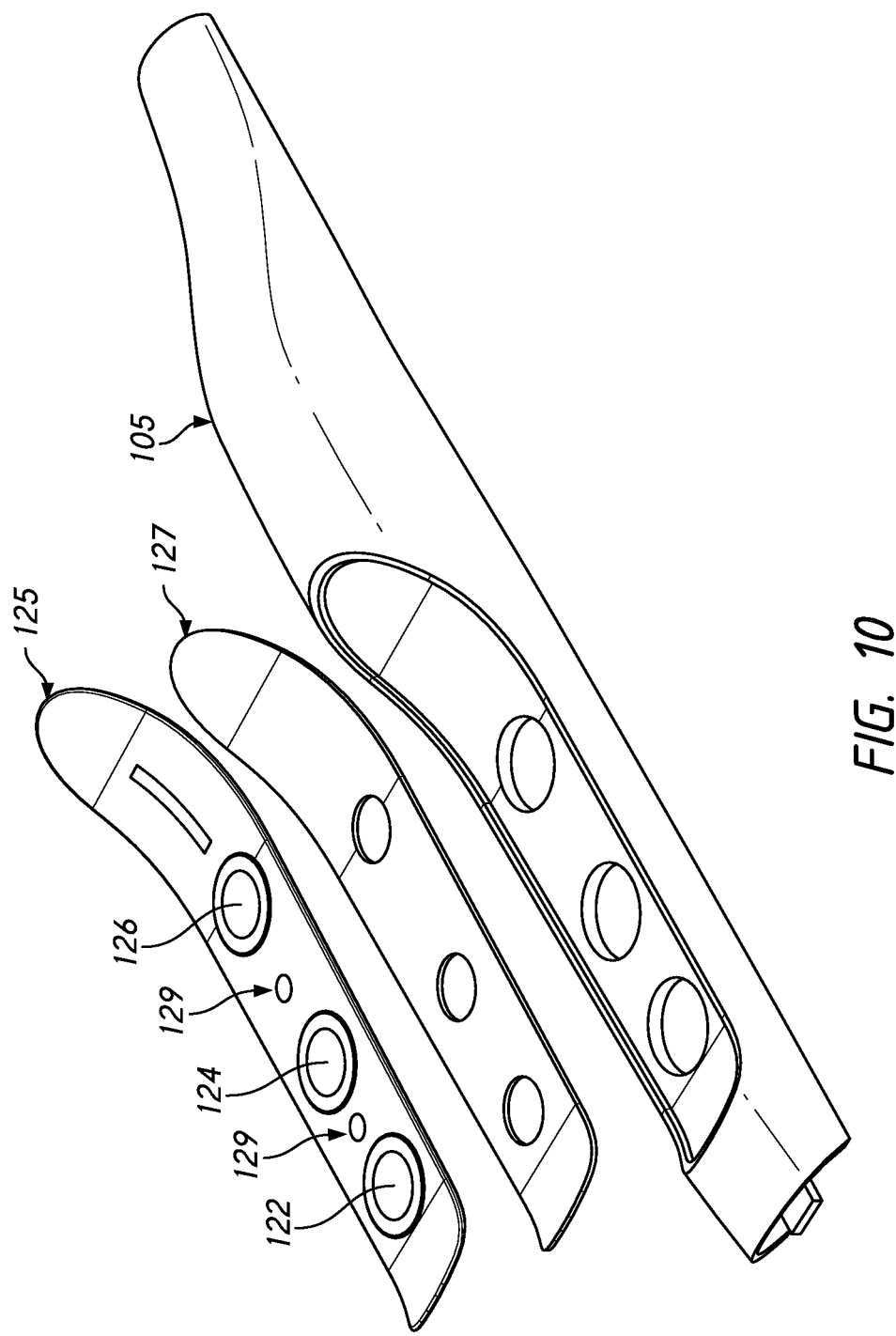
FIG. 10 is an exploded view of the upper shell of FIG. 9.
Figure 11:
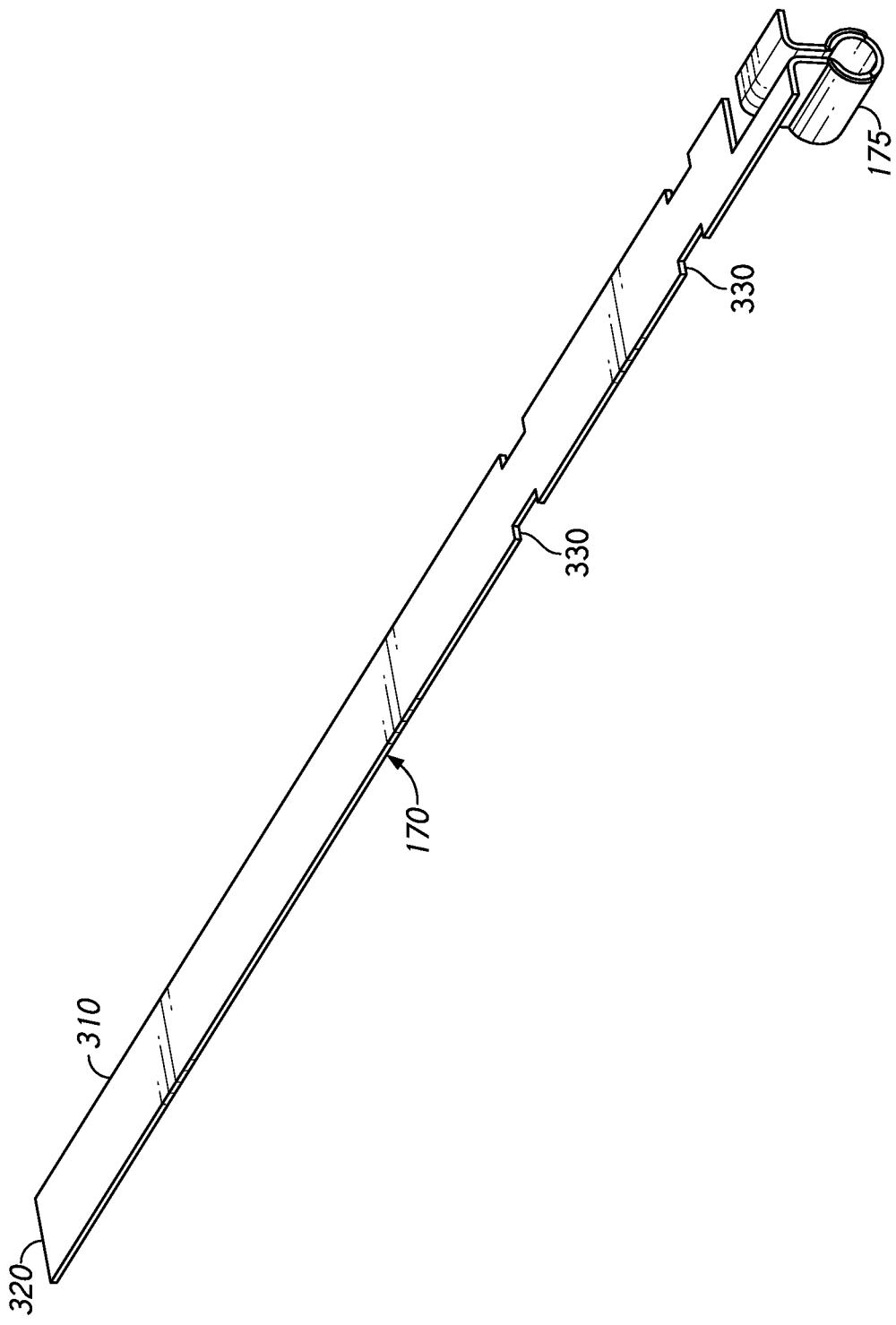
FIG. 11 is a top perspective view of a conductive rail and cauterizing tip mount according to an embodiment.
Figure 12:
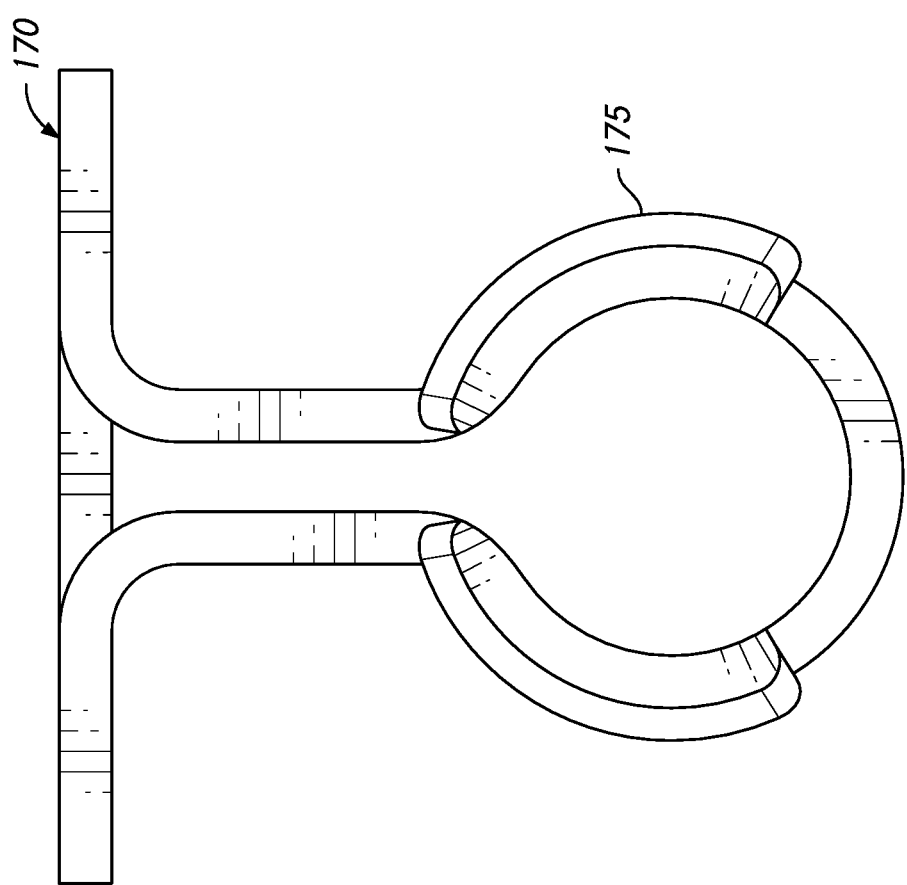
FIG. 12 is an end view of the cauterizing tip mount and conductive rail of FIG. 11.
Figure 13:
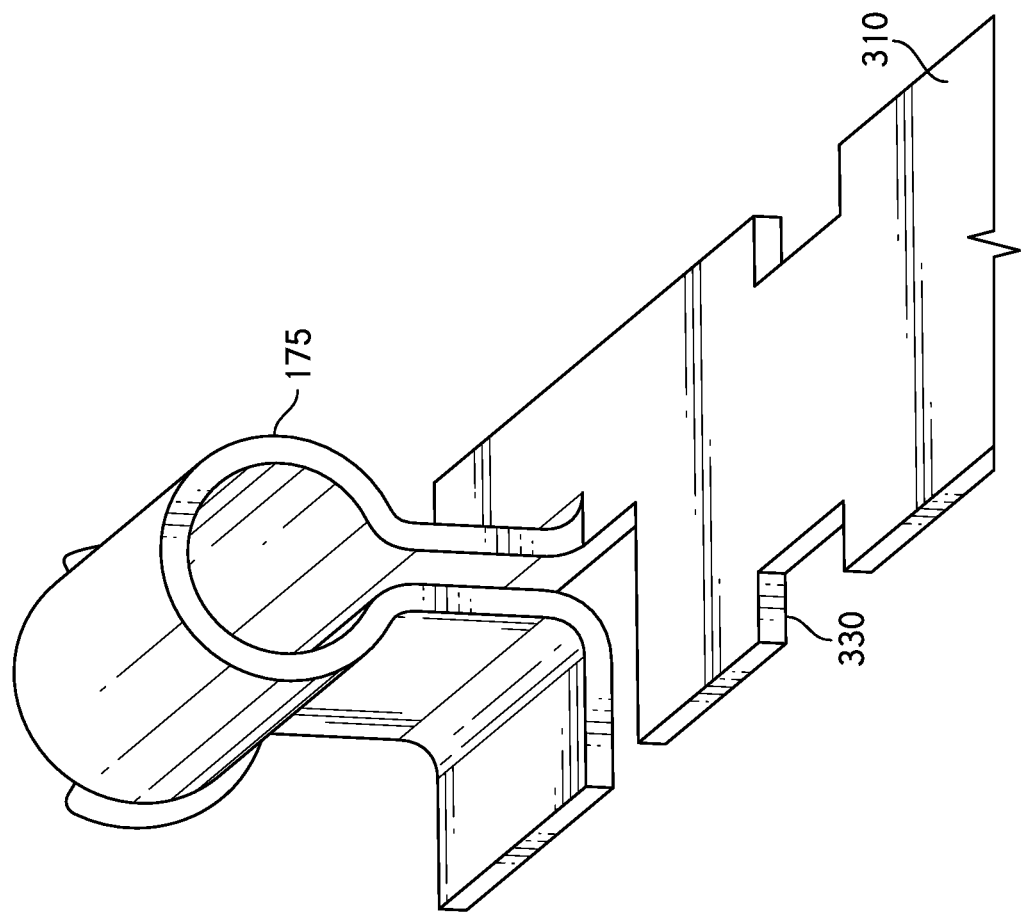
FIG. 13 is a partial, rear perspective view of the cauterizing tip mount and conductive rail of FIG. 11.

Referring to FIGS. 9 and 10 along with FIG. 8, the control panel 120 may include buttons 122, 124, and 126 with the underlying switch pads 132, 134, and 136 aligned accordingly. FIG. 10 may be a further embodiment of FIG. 9, which may include an indexing feature as discussed below. The button substrate 125 may include upward curved ends that follow the curved faces of the button area of upper casing half 105a as shown in FIG. 3B, blocking visibility of the internal components lying underneath. The casing upper half 105a includes holes 122a, 124a, and 126a for each of respective buttons 122, 124, and 126 to protrude through. In some embodiments, a double-sided water tight adhesive layer 127 may be positioned below the substrate 125 and the casing 105 providing a water tight seal to protect the electronics within the device 100. The substrate 125 may in some embodiments, include index features 129 (such as bumps or openings that provide a tactile indication of position) so that the user may feel where their finger (thumb) position is among the buttons. This allows the user to maintain focus on the operation at hand without needing to visually confirm what button is being pushed. While the drawings show that the indexes 129 have a same shape it will be understood that in some embodiments, the indexes 129 may have different shapes to differentiate between the positions between the buttons.

Referring now to FIGS. 15A and 15B, an alternate embodiment is shown as an electrocautery device 200. The device 200 may be similar to the device 100 except that the casing 250 provides an ergonomic shape that provides comfort when holding the device 200. The device 200 may include a rubber grip 255. Buttons 230, 240, and 260 may be contoured to align with the contours of the casing 250. A cauterizing tip 210 may telescope in and out as described above with the remaining telescoping elements and constant conductive connection remaining available during the telescoping operation.

Referring now to FIGS. 16-21 (and their sub-figures), alternate embodiments of switches that may be used in conjunction with embodiments described above is shown. Some embodiments may include a membrane type switch that would replace the buttons described above.

FIG. 16 shows a switch overlay system 400 according to an exemplary embodiment. The switch overlay system 400 may include a switch film assembly 405 that incorporates one or more switch areas 410, 420, and 430. In an exemplary embodiment, the system 400 may include a width of approximately 13.2 millimeters (mm) and a thickness of approximately 0.18 mm (FIG. 16B). For embodiments including a dome type switch, the thickness from the bottom of the film to the top of the dome may be approximately 0.25 mm (FIG. 16A).

FIG. 17 shows an enlarged cross-section of a switch area, for example switch area 410, and the film assembly 405 which may include a plurality of layers which can be seen in detail in FIGS. 18, 18A, and 18B. In an exemplary embodiment, the switch areas 410, 420, and 430 may be dome type switches. It will be understood that the switch areas 420 and 430 may be similar to switch area 410 and the description of switch area 410 may likewise represent switch areas 420 and 430. However, as will be appreciated, instead of single actuation buttons, overlays arranged in the embodiments discussed will allow a single piece interface with multiple activation points. This allows multiple functions (for example, cutting, coagulation mode, or lighting) from a single switch system. Aside from pure functionality, this also allows for variation of the finished product in the printed cosmetic and layout design. In addition, the switch areas 410, 420, and 430 may be considered as localized parts of the film assembly 405 except that elements specific to the switch areas may be described as separate from the film assembly 405 as noted. As will be further appreciated, the embodiments disclosed may protect the interior from inadvertent fluid entry. Instead of individual buttons that may each present the risk of a leak paths, the internal electronics are sealed from ingress of fluids and vapors. This increases electrical isolation from the environment. In addition, multiple functions may be incorporated yet safety increases because there is less chance of a leak path being present.

In an exemplary embodiment, the switch area 410 may be positioned over a PCB layer 470 which may include a trace or other conductive point (not shown) which registers a user's touch of the switch area 410. The PCB layer 470 may be similar to the PCB 130 described above. The switch area 410 may include for example, an embossed overlay layer 440, which may be for example polyester or another translucent soft material. Some embodiments may include graphics or color on the layer 440 for the user to identify a function associated with the switch area 410 (or likewise a different function associated with each of areas 420 and 430). Some embodiments may include a raised pad 445 in the layer 440. The raised pad 445 may be positioned over a metallic dome 460 (not necessarily present in other areas of the film assembly 405 that are not switch areas). The raised pad 445 may be contoured to approximately match the curve of the dome 460. Some embodiments may include a dome retainer layer 450 that includes an adhesive to attach the dome 460 to the overlying raised pad 445. The metallic dome 460 may be in direct contact with the underlying PCB layer 470 so that pressing down on the switch area 410 presses the raised part of the dome 460 into contact with an underlying metal contact point in the PCB 470 to create a circuit.

FIGS. 19, 19A, and 19B show an alternate embodiment of the system 400 that is used in an electrocautery system such as the embodiments described above. For sake of illustration the system 400 is shown only in conjunction with an upper casing 105a (see also FIG. 3B). The system 400 in FIGS. 19, 19A, and 19B may be the same as the system 400 in FIGS. 16-18 (and their sub-figures), except that in this embodiment, an actuator 480 may be positioned between the raised pad 445 and the dome 460. The actuator 480 may fill a gap between the pad 445 and dome 460 and may facilitate actuation of the dome 460 to the underlying PCB 470. The actuator 480 may be floating within the space or integrated into the PCB 470.

Referring now to FIGS. 20, 20A, and 20B, a membrane switch system 500 is shown applied to an electrocautery device (such as the device 100 described above). The membrane switch system 500 is similar to the system 400 except that the switch system 500 does not include an actuator between the dome 515 and the adhesive conductive layer or pad 520. Each switch (which may be referred to interchangeably as a "button" in some embodiments), may include the dome 515, the conductive layer 520, and the connection to the respective circuit element of the PCB 130 associated with the function of the switch. A top sealing layer 510 (membrane), may be positioned over the dome 515 and conductive layer 520 of each switch. A plurality of switches may be covered by a single layer 520. In some embodiments, the top sealing layer 510 may be flexible so that the layer indexes to the curves of the housing 105a. As will be appreciated, the arrangement provides a watertight seal shielding the electrical components in the housing 105a (for example, the PCB 130 below the switch) from exposure to fluids contacting the device. Similar to the description related to FIGS. 17, 18, 18A, and 18B, aspects of the embodiments in FIGS. 20, 20A, and 20B improve on the prior art by providing multiple functions under a single protective interface layer. In addition, less leak paths are introduced by virtue of using a single membrane layer (in some embodiments), to seal the underlying electronics from fluids in the environment.

Referring now to FIGS. 21 and 21A and 22, 22A, 22B, and 22C, a membrane switch system 600. The membrane switch 600 may be used for example, in the device 200 shown in FIGS. 15A and 15B. The membrane switch 600, as will be appreciated, removes some of the parts needed to operate the device 200 while maintaining a comfortable grip and feel for the user. The membrane switch system 600 may include a water tight sealed top layer 610 of polyester film which in some embodiments includes graphics or color to demarcate the area of the switch. A conductive pad 620 may be positioned below the top layer 610. As will be understood, each switch area designated to a function may include its own conductive pad 620, but for sake of illustration, only a single function/area is being described. A spacer layer 630 may be positioned below the top layer 610 and may include openings aligned with the conductive pad(s) 620. The spacer layer 630 may include a layer of PET between top and bottom layers of adhesive. In an exemplary embodiment, an area directly below the conductive pad 620 may remain free of adhesive to allow for better conduction with elements below the conductive pad 620. A layer 640 of circuit conductive ink(s) may be positioned below the conductive pad 620 and spacer layer 630. When assembled, the adhesive on the top and bottom of the spacer layer 630 may adhere to the overlying top layer 610 and underlying layer 640 of circuit conductive ink. In an exemplary embodiment, a layer 650 of printed circuit film may be positioned beneath the layer of 640 of circuit conductive ink. The layer 650 may be connected to a housing 660 which electrically connects to a PCB connector and PCB (not shown). In operation, when a user presses on the area of the membrane switch 600 with a designated function (see again FIGS. 15A and 15B), the underlying conductive pad 620 is pressed through the opening in the spacer layer 630 and into contact with the layer 640 of circuit conductive ink closing a circuit and generating a signal transmitted to the PCB.

Although the invention has been discussed with reference to specific embodiments, it is apparent and should be understood that the concept can be otherwise embodied to achieve the advantages discussed. Furthermore, the description is not intended to limit the invention to the form disclosed herein. Accordingly, variants and modifications consistent with the following teachings, skill, and knowledge of the relevant art, are within the scope of the present invention. The embodiments described herein are further intended to explain modes known for practicing the invention disclosed herewith and to enable others skilled in the art to utilize the invention in equivalent, or alternative embodiments and with various modifications considered necessary by the particular application(s) or use(s) of the present invention.

Those of skill in the art would appreciate that various components and blocks may be arranged differently (e.g., arranged in a different order, or partitioned in a different way) all without departing from the scope of the subject technology. For example, the rear base tube 145 may slide into the slider tube 150 to provide the same telescoping action described above. However, the functionality of the disclosed structure and its variations remains the same.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more.

Terms such as "top," "bottom," "front," "rear," "above," "below" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference. Similarly, an item disposed above another item may be located above or below the other item along a vertical, horizontal or diagonal direction; and an item disposed below another item may be located below or above the other item along a vertical, horizontal or diagonal direction. While some features are shown facing away from gravity, for example, the openings in the cutting tips or the blade edges of the sleeves shown, it will be understood that features can be rotated or positioned perpendicular to gravity and work to hold, knot, or cut a suture in the same way as shown.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U. S. C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An electrocautery system, comprising:
   a rear base tube;
   a slider tube coupled to the rear base tube, wherein the slider tube is configured to telescope toward a front nozzle tube or away from the rear base tube;
   a metal spring contact mounted to either the front nozzle tube or the rear base tube;
   a conductive rail mounted to an exterior surface of the slider tube, wherein the metal spring contact is disposed to make constant contact with the conductive rail as the slider tube telescopes toward or away from the rear base tube, the conductive rail formed of a flat conductive material disposed along a length of the exterior surface of the slider tube;
   a mount on a distal end of the conductive rail, the mount configured to receive a cauterizing tip; and
   a power line in electrical communication with the metal spring contact, the conductive rail, and the mount for providing power to the cauterizing tip during operation of the electrocautery system, wherein
   the slider tube and the rear base tube are hollow and define a fluid passage through a distal end of the slider tube to a proximal end of the rear base tube,
   the proximal end of the rear base tube is configured to receive a vacuum source, and
   fluid in the fluid passage is prevented from contacting the metal spring contact or the conductive rail.

2. The electrocautery system of claim 1, further comprising an electronics board including electronics, the metal spring contact being connected to the power line through the electronics board.

3. The electrocautery system of claim 1, further comprising conductive break points in predetermined locations of the conductive rail.

4. The electrocautery system of claim 1, wherein, a connection between the metal spring contact and the electronics board is static.

5. The electrocautery system of claim 1, further comprising a slider tab connected to the slider tube, wherein operation of the slider tab telescopes the slider tube toward or away from the rear base.

6. The electrocautery system of claim 1, wherein, the metal spring contact includes a clip affixing the metal spring contact to the rear base tube.

7. An electrocautery system, comprising:
a rear base tube;
a slider tube coupled to the rear base tube, wherein the slider tube is configured to telescope toward a front nozzle tube or away from the rear base tube;
a metal spring contact mounted to either the front nozzle tube or the rear base tube;
a conductive rail mounted to an exterior surface of the slider tube, wherein the metal spring contact is disposed to make constant contact with the conductive rail as the slider tube telescopes toward or away from the rear base tube, the conductive rail formed of a flat conductive material disposed along a length of the exterior surface of the slider tube;
a mount on a distal end of the conductive rail, the mount configured to receive a cauterizing tip;
a fluid passage through a distal end of the slider tube to a proximal end of the rear base tube, the fluid passage sealed from the metal spring contact and the conductive rail, wherein fluid in the fluid passage is prevented from contacting the metal spring contact or the conductive rail; and
a power line in electrical communication with the metal spring contact, the conductive rail, and the mount for providing power to the cauterizing tip during operation of the electrocautery system.

8. The electrocautery system of claim 7, further comprising a nozzle on the distal end of the slider tube, wherein the cauterizing tip, when received by the mount, telescopes in and out of the nozzle as the slider tube telescopes toward or away from the rear base tube.

9. The electrocautery system of claim 7, wherein the slider tube is non-conductive.

10. The electrocautery system of claim 9, wherein the cauterizing tip, when received by the mount is external from the fluid passage within the slider tube.

11. The electrocautery system of claim 10, wherein the conductive rail is mounted on an external surface of the slider tube.

12. The electrocautery system of claim 11, further comprising an electronics board including electronics, the metal spring contact being connected to the power line through the electronics board.

13. The electrocautery system of claim 12, further comprising conductive break points in predetermined locations of the conductive rail.

14. The electrocautery system of claim 13, wherein, the metal spring contact includes a clip affixing the metal spring contact to the rear base tube.

15. An electrocautery system, comprising:
a rear base tube;
a slider tube coupled to the rear base tube, wherein the slider tube is configured to telescope toward a front nozzle tube or away from the rear base tube;
a static metal contact mounted to either the front nozzle tube or the rear base tube;
an elongated metal contact mounted to an exterior surface of the slider tube, wherein the static metal contact is disposed to make constant contact with the elongated metal contact as the slider tube telescopes toward or away from the rear base tube, the elongated metal contact formed of a flat conductive material disposed along a length of the exterior surface of the slider tube;
a mount on a distal end of the slider tube, the mount configured to receive a cauterizing tip;
a conductive connection between the cauterizing tip and the elongated metal contact; and
a power line in electrical communication with the static metal contact, the elongated metal contact, and the mount for providing power to the cauterizing tip during operation of the electrocautery system, wherein
the slider tube and the rear base tube are hollow and define a fluid passage through the distal end of the slider tube to a proximal end of the rear base tube,
the proximal end of the rear base tube is configured to receive a vacuum source, and
fluid in the fluid passage is prevented from contacting the metal spring contact or the conductive rail.

16. The electrocautery system of claim 15, wherein the mount is conductive.

17. The electrocautery system of claim 16, wherein the slider tube is non-conductive.

18. The electrocautery system of claim 15, wherein the cauterizing tip, when received by the mount is external from the fluid passage within the slider tube.

* * * * *